United States Patent
Kojima et al.

(10) Patent No.: US 10,413,252 B2
(45) Date of Patent: Sep. 17, 2019

(54) MEDICAL IMAGE DISPLAY APPARATUS AND MEDICAL IMAGE MANAGEMENT SYSTEM

(71) Applicant: Toshiba Medical Systems Corporation, Otawara-shi (JP)

(72) Inventors: Takayuki Kojima, Sakura (JP);
Kensuke Shinoda, Sakura (JP);
Takumi Kaneko, Nasushiobara (JP);
Hideaki Kobayashi, Otawara (JP);
Shinya Sato, Nasushiobara (JP);
Satoshi Okuyama, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 0 days.

(21) Appl. No.: 15/492,624

(22) Filed: Apr. 20, 2017

(65) Prior Publication Data
US 2017/0303865 A1    Oct. 26, 2017

(30) Foreign Application Priority Data
Apr. 21, 2016 (JP) ................. 2016-085484

(51) Int. Cl.
*A61B 5/00* (2006.01)
*G06T 7/00* (2017.01)
*G06T 11/00* (2006.01)
*G06T 11/60* (2006.01)

(52) U.S. Cl.
CPC .......... *A61B 5/742* (2013.01); *G06T 7/0012* (2013.01); *G06T 11/60* (2013.01); *G06T 2200/24* (2013.01); *G06T 2207/10081* (2013.01); *G06T 2210/41* (2013.01)

(58) Field of Classification Search
None
See application file for complete search history.

(56) References Cited

U.S. PATENT DOCUMENTS

2010/0054566 A1* 3/2010 Toda ............... G06F 19/321
382/131

FOREIGN PATENT DOCUMENTS

| JP | 2006-333889 | | 12/2006 |
| JP | 2015-128472 | | 7/2015 |
| JP | 2015128472 | A * | 7/2015 |

* cited by examiner

*Primary Examiner* — Yingchun He
(74) *Attorney, Agent, or Firm* — Oblon, McClelland, Maier & Neustadt, L.L.P.

(57) ABSTRACT

According to one embodiment, a medical image display apparatus comprises reception circuitry, a storage, and control circuitry. The reception circuitry configured to receive at least one medical images imaged by a medical imaging apparatus, and first progress information indicating that image inspection for the at least one medical images is in progress in a medical image inspection apparatus, and receive second progress information indicating completion of the image inspection for the at least one medical images. The storage configured to store the at least one medical images and the first progress information. The control circuitry configured to update the stored first progress information to the second progress information, if the second progress information is received.

5 Claims, 8 Drawing Sheets

MEDICAL IMAGE DISPLAY APPARATUS AND MEDICAL IMAGE MANAGEMENT SYSTEM

CROSS-REFERENCE TO RELATED APPLICATIONS

This application is based upon and claims the benefit of priority from Japanese Patent Application No. 2016-085484, filed Apr. 21, 2016, the entire contents of which are incorporated herein by reference.

FIELD

An embodiment of the present invention relates to a medical image display apparatus and a medical image management system.

BACKGROUND

Generally, in a medical imaging apparatus which performs medical imaging, or a computer such as a medical image processing apparatus which is set separately from the medical imaging apparatus, an operation to confirm whether a medical image acquired by the medical imaging is available for image interpretation is performed. This confirmation operation is called image inspection, and the medical image processing apparatus separately set from the medical imaging apparatus is called a medical image inspection apparatus. After image inspection of a medical image, the medical image that was subjected to the image inspection is transferred to a medical image display apparatus to browse the medical image, and to a computer such as a medical image interpretation apparatus to perform image interpretation. Image interpretation of the transferred medical image is performed by an image interpreting doctor. Thus, the image interpreting doctor must wait until completion of the image inspection, the image transmission after the image inspection, and processing to make the image available by applications. Furthermore, in the process of transferring a medical image after completion of the image inspection to the image interpretation, display conditions, such as a window width, a window level, and GSPS (Gray-Scale Presentation Statement) may be adjusted, or an area unnecessary for the diagnosis may be designated or deleted. Accordingly, the inspection efficiency is lowered.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

In general, according to one embodiment, a medical image display apparatus comprises reception circuitry, a storage, and control circuitry. The reception circuitry configured to receive at least one medical images imaged by a medical imaging apparatus, and first progress information indicating that image inspection for the at least one medical images is in progress in a medical image inspection apparatus, and receive second progress information indicating completion of the image inspection for the at least one medical images. The storage configured to store the at least one medical images and the first progress information. The control circuitry configured to update the stored first progress information to the second progress information, if the second progress information is received.

Hereinafter, a medical image management system according to an embodiment will be described below with reference to the accompanying drawings.

Figure 1:
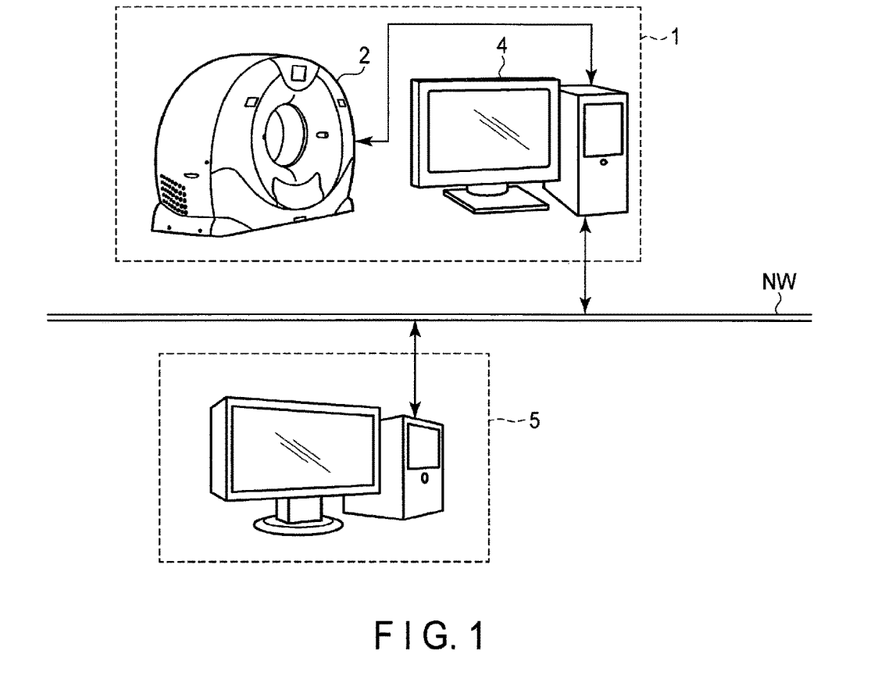
FIG. 1 is a diagram showing a medical image management system according to an embodiment.

FIG. 1 is a diagram showing a medical image management system according to the embodiment. The medical image management system shown in FIG. 1 includes a medical image diagnosis apparatus 1 and a medical image display apparatus 5. For example, the medical image diagnosis apparatus 1 performs medical imaging for a subject S and generates a medical image relating to the subject S. Furthermore, the medical image display apparatus 5 of the embodiment displays the medical image for medical image interpretation or the like.

Figure 2:
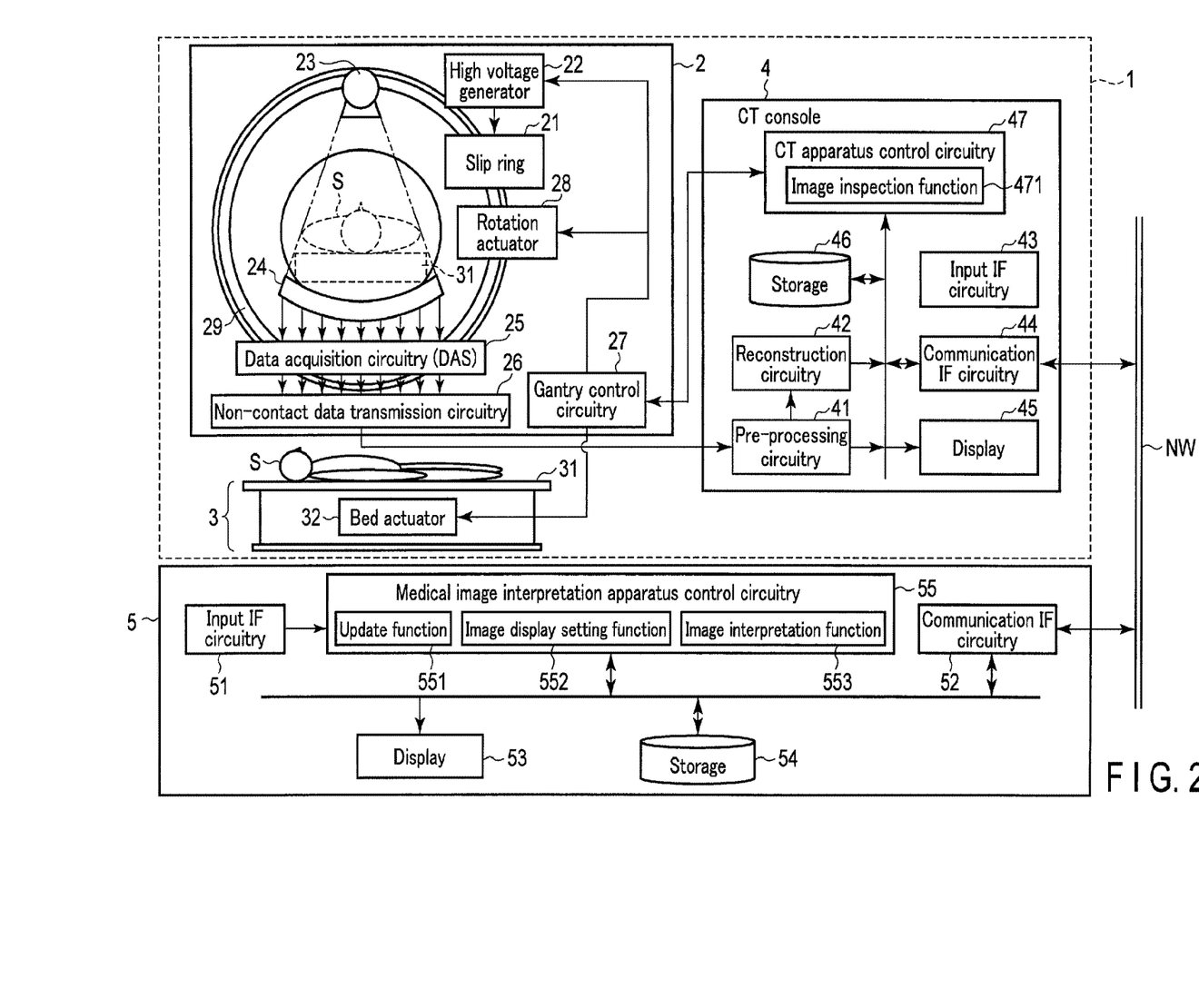
FIG. 2 is a block diagram showing a configuration of an X-ray CT apparatus and a medical image interpretation apparatus according to the embodiment.

The medical image diagnosis apparatus 1 may be any modality that can generate a medical image. For example, it may be a CT (Computed Tomography) apparatus, a magnetic resonance imaging (MRI) apparatus, an X-ray diagnosis apparatus, a nuclear medicine diagnosis apparatus, or a diagnostic ultrasound imaging apparatus. In the following description of the embodiment, the medical image diagnosis apparatus 1 is described as the X-ray CT apparatus 1. The medical image display apparatus 5 may be any type of computer that is connected to the medical image diagnosis apparatus 1. In the following description of the embodiment, the medical image display apparatus 5 is described as the medical image interpretation apparatus 5. The X-ray CT apparatus 1 and the medical image interpretation apparatus 5 are connected to each other via a network NW. The X-ray CT apparatus 1 transfers a generated CT image constituting volume data to the medical image interpretation apparatus 5. The medical image interpretation apparatus 5 performs image interpretation based on the CT image. The X-ray CT apparatus 1 and the medical image interpretation apparatus 5 according to the embodiment will be described in detail. FIG. 2 is a block diagram showing the configuration of the X-ray CT apparatus 1 and the medical image interpretation apparatus 5 according to the embodiment. First, the X-ray CT apparatus 1 will be explained.

As shown in FIG. 2, the X-ray CT apparatus 1 includes a gantry 2, a bed 3, and a CT console 4. The gantry 2 includes a slip ring 21, a high voltage generator 22, an X-ray tube 23, an X-ray detector 24, data acquisition circuitry (DAS: Data Acquisition System) 25, non-contact data transmission circuitry 26, gantry control circuitry 27, and a rotation actuator (electric motor) 28. A top plate 31, on which the subject S can lie, is inserted through a bore of a rotation ring 29. The top plate 31 is supported by the bed 3 so as to be movable along a central axis of the rotation ring 29. The top plate 31 is positioned so that a body axis of the subject S laid on the top plate 31 coincides with the central axis of the rotation ring 29.

The high voltage generator 22 generates an X-ray tube voltage to be applied to the X-ray tube 23 and an X-ray tube current (filament current) to be supplied to the X-ray tube 23 under control of the CT console 4 via the gantry control circuitry 27. The X-ray tube 23 receives the application of the X-ray tube voltage and supply of the X-ray tube current from the high voltage generator 22 via the slip ring 21, and radiates X-rays from a focus of the X-rays to the subject S laid on the top plate 31. The X-ray detector 24 is attached to a position on the opposite side of a rotation axis of the rotation ring 29 from the X-ray tube 23. The X-ray detector 24 includes a plurality of detection elements that detect X-rays. The detection elements are arranged two dimensionally in a channel direction and a column direction. The DAS 25 is connected to an output side of the X-ray detector 24.

The DAS 25 includes an IV converter that converts a current signal of each element of the X-ray detector 24 to a voltage signal, an integrator that periodically integrates the voltage signal in synchronism with radiation periods of X rays, an amplifier that amplifies an output signal of the integrator, and an analog-to-digital converter that converts an output signal of the amplifier to a digital signal. The DAS 25 transmits output data (raw data) to the CT console 4 through the non-contact data transmission circuitry 26 using magnetic transmission/reception or optical transmission/reception.

The gantry control circuitry 27 includes a processor, such as a CPU (Central Processing Unit) and a MPU (Micro Processing Unit), and a memory, such as a ROM (Read Only Memory) and a RAM (Random Access Memory), as hardware resources. The processor of the gantry control circuitry 27 integrally controls operations of the respective components provided in the gantry 2 in accordance with a control signal output from the CT console 4. The processor of the gantry control circuitry 27 also controls operations of the respective components provided in the bed 3.

Specifically, the gantry control circuitry 27 controls the supply of power from the high voltage generator 22 to the slip ring 21 to perform imaging in accordance with a predetermined scan sequence. The gantry control circuitry 27 also rotates the rotation ring 29 by controlling the rotation actuator 28. The gantry control circuitry 27 moves the top plate 31 by controlling the bed actuator 32 via the gantry control circuitry 27. The subject S laid on the top plate 31 is moved along the direction of the body axis by the movement of the top plate 31.

The bed 3 includes the top plate 31 on which the subject S is laid and the bed actuator 32. The bed actuator 32 moves the top plate 31 under control of the gantry control circuitry 27 or under control of the CT console 4 via the gantry control circuitry 27. For example, the bed actuator 32 moves the top plate 31 in a direction perpendicular to the subject S so that the body axis of the subject S laid on the top plate 31 coincides with the central axis of the rotation ring 29. The bed actuator 32 also moves the top plate 31 in a direction along the body axis of the subject S in accordance with X-ray CT imaging performed by using the gantry 2.

The CT console 4 includes pre-processing circuitry 41, reconstruction circuitry 42, input interface (IF) circuitry 43, communication interface (IF) circuitry 44, a display 45, a storage 46, and CT apparatus control circuitry 47.

The pre-processing circuitry 41 performs pre-processing on the raw data output from the non-contact data transmission circuitry 26. The pre-processing includes, for example, processing for logarithmic conversion of raw data, processing for correcting non-uniformity in sensitivity of channels, and processing for correcting an extreme decrease in signal intensity due to a strong absorber of X-rays, in particular, a metal part, or processing for correcting signal omission. The pre-processing circuitry 41 transfers the pre-processed raw data (called projection data) to the reconstruction circuitry 42 and the storage 46.

The reconstruction circuitry 42 includes a predetermined memory and a predetermined processor. The reconstruction circuitry 42 reconstructs, for example, almost cylindrical volume data based on a projection data set transmitted from the pre-processing circuitry 41. The volume data is composed of a plurality of CT images relating to a plurality of slices arranged in a slice direction. The reconstruction circuitry 42 transmits the almost cylindrical volume data to the storage 46. The reconstruction circuitry 42 reconstructs a two-dimensional CT image (a tomographic image, hereinafter simply referred to as a CT image) from the projection image data set. The reconstruction circuitry 42 transmits the reconstructed CT image to the storage 46.

The input interface circuitry 43 includes at least a trackball, a switch button, a mouse, a keyboard, a touch pad through which an input operation can be carried out by a touch of an operation surface, a touch panel display, which is an integrated combination of a display window and a touch pad, etc. The input interface circuitry 43 converts an input operation received from an operator to an electric signal, and outputs the electric signal to the CT apparatus control circuitry 47. In this embodiment, the input interface circuitry 43 is not limited to circuitry provided with a physical operation component, such as a trackball, a switch button, a mouse, and a keyboard. For example, the input interface circuitry 43 also includes electric signal processing circuitry that receives an electric signal corresponding to an input operation through an external input device separate from the apparatus, and outputs the electric signal to the CT apparatus control circuitry 47. The communication interface circuitry 44 communicates with the medical image interpretation apparatus 5 by wire or wirelessly.

The display 45 displays various data, the CT image, etc. in accordance with control by the CT apparatus control circuitry 47. Specifically, the display 45 includes display interface circuitry and a display device. The display interface circuitry converts data representing a display target to a video signal. A display signal is supplied to the display device. The display device displays the video signal representing the display target. For example, the display 45 displays a CT image stored in the storage 46 in accordance with an input instruction input via the input interface circuitry 43 by a viewer who browses the CT image during image interpretation or the like in the CT console 4. As the display device, for example, a CRT display (Cathode Ray Tube Display), a liquid crystal display (LCD), an organic electro luminescence display (OELD), a plasma display, or any other display known in this technical field is available as appropriate.

The storage 46 is an HDD (Hard Disk Drive), an SSD (Solid State Drive), etc., which can store relatively large volumes of data. For example, the storage 46 stores the volume data and CT images reconstructed by the reconstruction circuitry 42. Besides a magnetic disc such as the HDD, a magnetic optical disc or an optical disc such as a CD (Compact Disc) and a DVD (Digital Versatile Disc) may be used as the storage 46. A storage area of the storage 46 may be within the X-ray CT apparatus 1 or within an external storage device that is connected to via the network NW. The storage 46 stores an image inspection program according to this embodiment.

The CT apparatus control circuitry 47 includes a processor, such as a CPU (Central Processing Unit) and an MPU (Micro Processing Unit), and a memory, such as a ROM (Read Only Memory) and a RAM (Random Access Memory), as hardware resources. The memory of the CT apparatus control circuitry 47 temporarily stores the image inspection program read from the storage 46. The processor of the CT apparatus control circuitry 47 realizes an image inspection function 471 by executing the image inspection program stored in the memory. By realizing the image inspection function 471, the CT apparatus control circuitry 47 displays on the display 45 an image inspection operation window to perform image inspection of the stored CT image. Furthermore, the CT apparatus control circuitry 47 transfers the CT images stored in the storage 46 to the medical image interpretation apparatus 5 via the communication interface circuitry 44. At this time, the CT apparatus control circuitry 47 appends image inspection progress information representing a status of progress of the image inspection of each of the CT images. For example, the CT apparatus control circuitry 47 appends image inspection progress information to the CT image by adding a note indicating that the image is under image inspection to a study comment, adding a text annotation indicating that the image is under image inspection, or adding a flag indicating that the image is under medical image inspection to a private tag. Next, the medical image interpretation apparatus 5 of this embodiment will be explained. The medical image interpretation apparatus 5 shown in FIG. 2 includes input interface (IF) circuitry 51, communication interface (IF) circuitry 52, a display 53, a storage 54, and medical image interpretation apparatus control circuitry 55.

The input interface circuitry 51 includes at least a trackball, a switch button, a mouse, a keyboard, a touch pad through which an input operation can be carried out by a touch of an operation surface, a touch panel display, which is an integrated combination of a display window and a touch pad, etc. The input interface circuitry 51 converts an input operation received from an operator to an electric signal, and outputs the electric signal to the medical image interpretation apparatus control circuitry 55. In this embodiment, the input interface circuitry 51 is not limited to circuitry provided with a physical operation component, such as a trackball, a switch button, a mouse, and a keyboard. For example, the input interface circuitry 51 also includes electric signal processing circuitry that receives an electric signal corresponding to an input operation through an external input device separate from the apparatus, and outputs the electric signal to the medical image interpretation apparatus control circuitry 55. The communication interface circuitry 52 communicates with the CT console 4 by wire or wirelessly.

The display 53 displays various data, the transferred CT image, etc. in accordance with control by the medical image interpretation apparatus control circuitry 55. Specifically, the display 53 includes display interface circuitry and a display device. The display interface circuitry converts data representing a display target to a video signal. A display signal is supplied to the display device. The display device displays the video signal representing the display target. For example, the display 53 displays a CT image stored in the storage 54 in accordance with an input instruction input via the input interface circuitry 51 by a viewer who browses the CT image during image interpretation or the like in the medical image interpretation apparatus 5. As the display device, for example, a CRT display (Cathode Ray Tube Display), a liquid crystal display (LCD), an organic electro luminescence display (OELD), a plasma display, or any other display known in this technical field is available as appropriate.

The storage 54 is an HDD, an SSD, etc., which can store relatively large volumes of data. For example, the storage 54 stores CT images transferred from the CT console 4. Besides a magnetic disc such as the HDD, a magnetic optical disc or an optical disc, such as a CD and a DVD, may be used as the storage 54. A storage area of the storage 54 may be within an external storage device that is connected to via the network NW. The storage 54 stores an update program, a display setting program, and an image interpretation program according to this embodiment.

The medical image interpretation apparatus control circuitry 55 includes a processor, such as a CPU and an MPU, and a memory, such as a ROM and a RAM, as hardware resources. The memory of the medical image interpretation apparatus control circuitry 55 temporarily stores the update program read from the storage 54. The processor of the medical image interpretation apparatus control circuitry 55 realizes an update function 551 by executing the update program stored in the memory. By realizing the update function 551, the medical image interpretation apparatus control circuitry 55 updates the image inspection progress information stored in the storage 54 in accordance with a progress of the image inspection of a medical image in the CT console 4. The memory of the medical image interpretation apparatus control circuitry 55 temporarily stores an image restoration program read from the storage 54. The processor of the medical image interpretation apparatus control circuitry 55 realizes an image display setting function 552 by executing the image restoration program stored in the memory. By realizing the image display setting function 552, the medical image interpretation apparatus control circuitry 55 performs predetermined processing for the CT image transferred from the CT console 4 depending on whether or not image interpretation is possible based on the image inspection result in the CT console 4. The memory of the medical image interpretation apparatus control circuitry 55 temporarily stores the image interpretation program read from the storage 54. The processor of the medical image interpretation apparatus control circuitry 55 realizes an image interpretation function 553 by executing the image interpretation program stored in the memory. The medical image interpretation apparatus control circuitry 55 executes image interpretation of the transferred CT image by realizing the image interpretation function 553.

A flow from CT image acquisition to generation of an image interpretation report in the medical image management system according to the embodiment will be detailed below.

(Ordinary Workflow)

Figure 3:
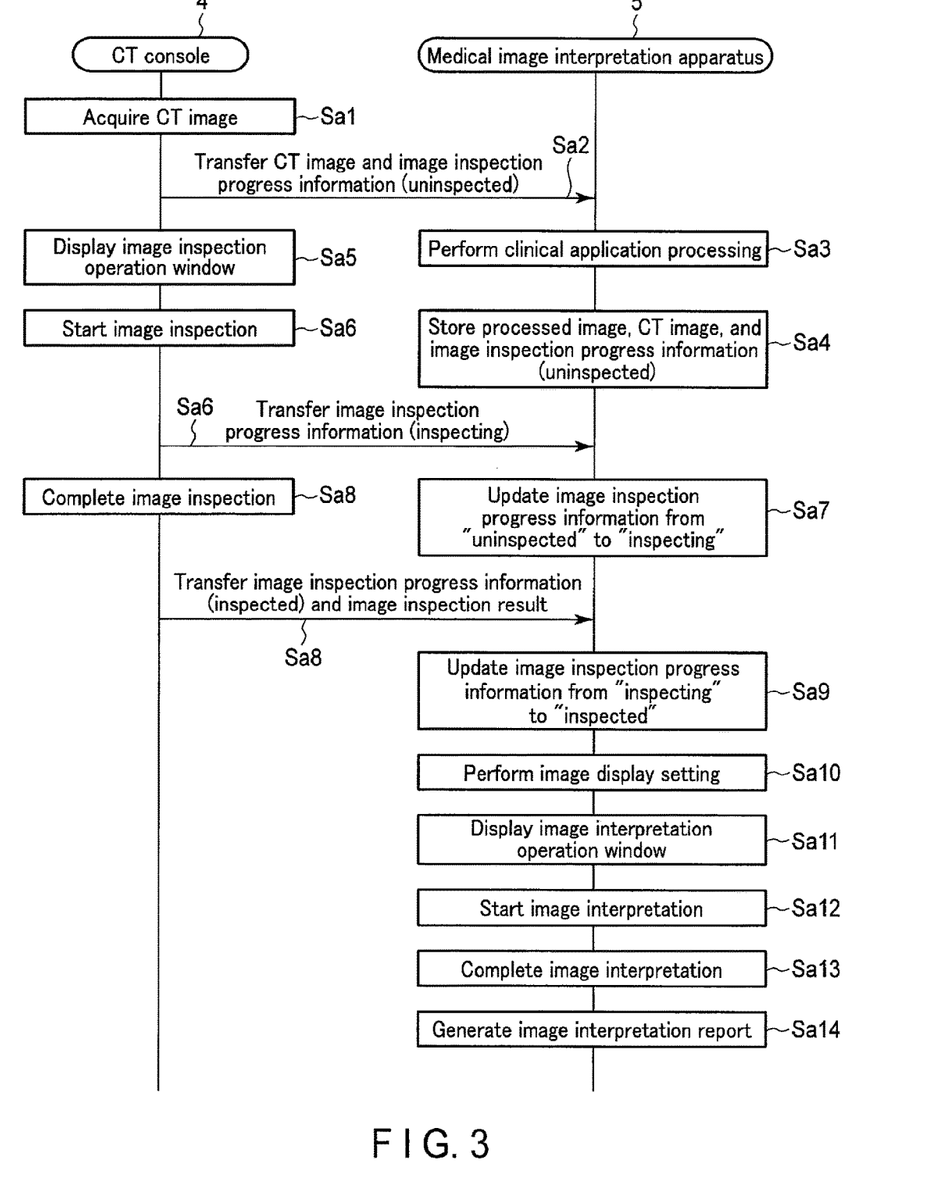
FIG. 3 is a flowchart showing a flow from CT image acquisition to generation of an image interpretation report in the medical image management system according to the embodiment.

FIG. 3 is a flowchart showing a flow from CT image acquisition to generation of an image interpretation report in the medical image management system according to the embodiment. In FIG. 3, an ordinary workflow of this embodiment is illustrated.

As shown in FIG. 3, in step Sa1, the CT apparatus control circuitry 47 acquires a CT image stored in the storage 46. In step Sa2, the CT apparatus control circuitry 47 transfers the CT image and progress of the image inspection corresponding to the CT image to the medical image interpretation apparatus 5 before starting the image inspection. In step Sa2, the CT apparatus control circuitry 47 transfers "image inspection progress information (uninspected)" as image inspection progress information indicative of progress of the image inspection. In step Sa3, the transferred CT image is subjected to predetermined processing by, for example, a clinical application, and converted to a format that can be handled by the medical image interpretation apparatus 5. If necessary, a processed image for use in image interpretation in the medical image interpretation apparatus 5 may be generated from the CT image.

Figure 4:
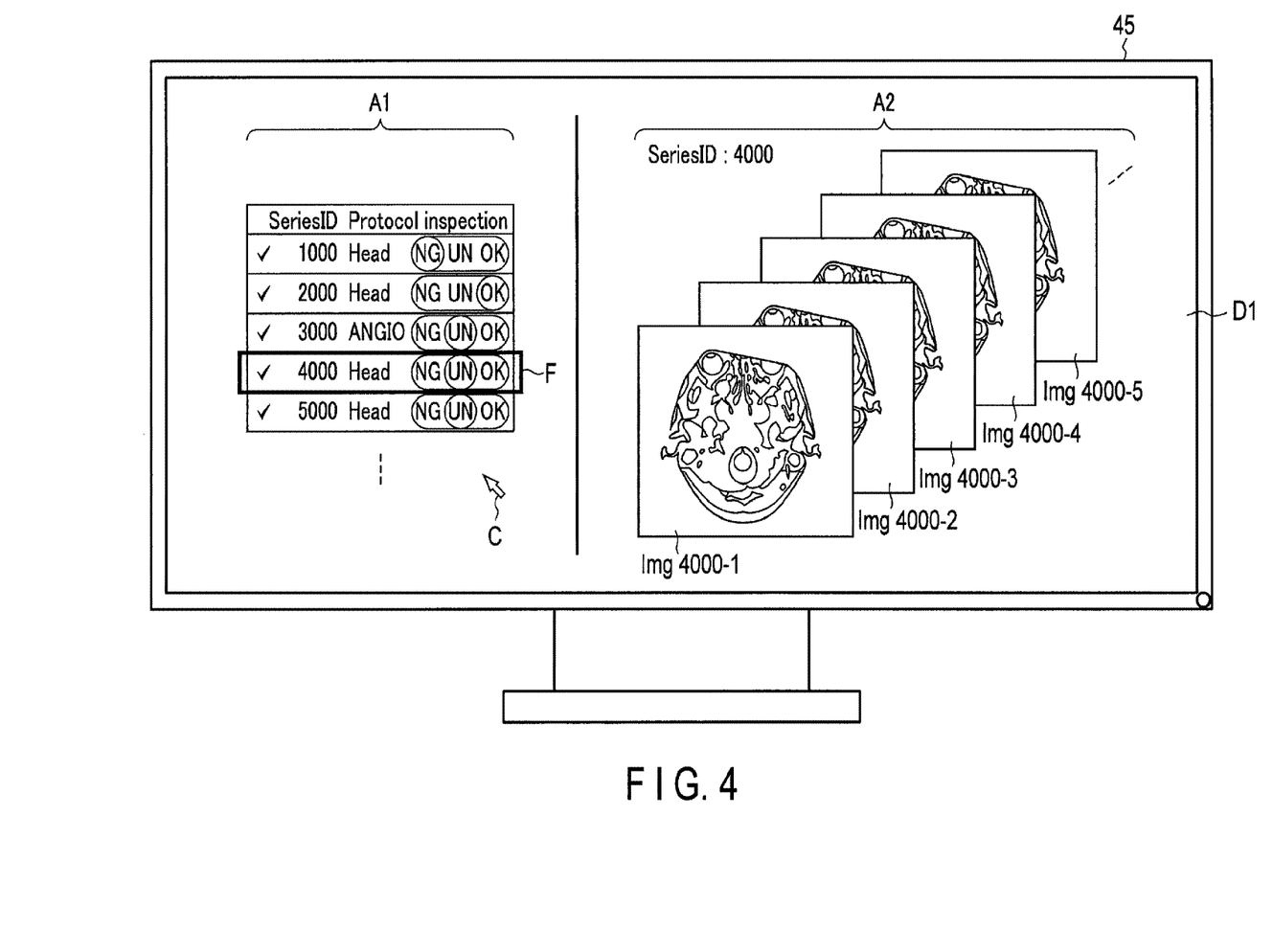
FIG. 4 is a diagram showing an example of an image inspection window displayed in a display shown in FIG. 2.

In step Sa4, the storage 54 stores the processed image, the transferred CT image, and the image inspection progress information (uninspected). In parallel with the transfer of the CT image, in step Say, the CT apparatus control circuitry 47 displays an image inspection operation window as the image inspection function 471 in the display 45. In step Sa6, the image inspection operation window is operated via the input interface circuitry 43 by a radiology technologist or the like, who performs image inspection, and image inspection for the CT image by a user (for example, the radiology technologist) is started. The image inspection includes adjustment of display conditions, such as a window width, a window level, and GSPS adjustment, and designation and deletion of an area unnecessary for the diagnosis. FIG. 4 is a diagram showing an example of an image inspection operation window displayed in the display 45 shown in FIG. 2. As shown in FIG. 4, the display 45 provides a display area A1 and a display area A2 on a display window D1. The display area A1 displays progress of image inspection of the CT image. For example, the display area A1 displays a series ID appended to a series of imaged CT images, a protocol (Head, ANGIO, etc., shown in FIG. 4) appended to the image, such as an imaged part or a type of medical imaging, and progress of the image inspection (image interpretation NG, uninspected, image interpretation OK, etc. shown in FIG. 4). The display area A2 displays a series of CT images corresponding to the series ID that is framed by a selection frame F selected by a cursor C. For example, as shown in FIG. 4, the display area A2 displays the series of CT images Img 4000-1, Img 4000-2, . . . corresponding to "Series ID: 4000" selected by the cursor C. The display window D1 shown in FIG. 4 is an example, and the embodiment is not limited to the display window shown in FIG. 4. For example, the display window may display "transmission" and "transmission cancel" buttons. Alternatively, the display window may display only a "transmission" button, in which case if the user completes image inspection without pushing the "transmission" button, cancellation of the operation may be transmitted to the CT apparatus control circuitry 47. After starting the image inspection, the CT apparatus control circuitry 47 transfers current image inspection progress information to the medical image interpretation apparatus 5.

In step Sa6, the CT apparatus control circuitry 47 transfers "image inspection progress information (inspecting)" as the current image inspection progress information. In step Sa7, the medical image interpretation apparatus control circuitry 55 updates the image inspection progress information stored in the storage 54 from "uninspected" to "inspecting" based on the image inspection progress information (inspecting) transferred from the CT console 4 as the update function 551. In step Sa8, if the image inspection in the CT console 4 is completed, the CT apparatus control circuitry 47 transfers the current image inspection progress information and an image inspection result to the medical image interpretation apparatus 5. For example, in step Sa8, the CT apparatus control circuitry 47 transfers "inspected" as the image inspection progress information. The CT apparatus control circuitry 47 also transfers "suitable for image interpretation" or "unsuitable for image interpretation" as the image inspection result in association with a UID (Unique IDentifier) appended to the CT image corresponding to the image inspection result.

In step Sa9, the medical image interpretation apparatus control circuitry 55 updates the image inspection progress information stored in the storage 54 from "inspecting" to "inspected" based on the image inspection progress information (inspected) transferred from the CT console 4 as the update function 551. In step Sa10, upon updating the image inspection progress information stored in the storage 54 from "inspecting" to "inspected", the medical image interpretation apparatus control circuitry 55 executes image display setting for the CT image stored in the storage 54, based on the transferred image inspection result as the image display setting function 552. For example, the medical image interpretation apparatus control circuitry 55 specifies an image determined to be "suitable for image interpretation" in the CT console 4 based on the transferred image inspection result (suitable for image interpretation) and the UID. The image determined to be "suitable for image interpretation" is displayed in the display 53, or displayed in the display 53 with second display information (a mark) representing that the image is suitable for image interpretation. The medical image interpretation apparatus control circuitry 55 also specifies an image determined to be "unsuitable for image interpretation" based on the transferred image inspection result (unsuitable for image interpretation) and the UID. The image determined to be "unsuitable for image interpretation" is not displayed in the display 53, or displayed in the display 53 with first display information (a mark) representing that the image is unsuitable for image interpretation, or deleted from the storage 54. If a mark corresponding to an image inspection result is displayed, the marks corresponding to image inspection results are stored in advance in the storage 54, and the corresponding mark for each image to be subjected to image display setting is read from the storage 54 and appended to the image.

Figure 5:
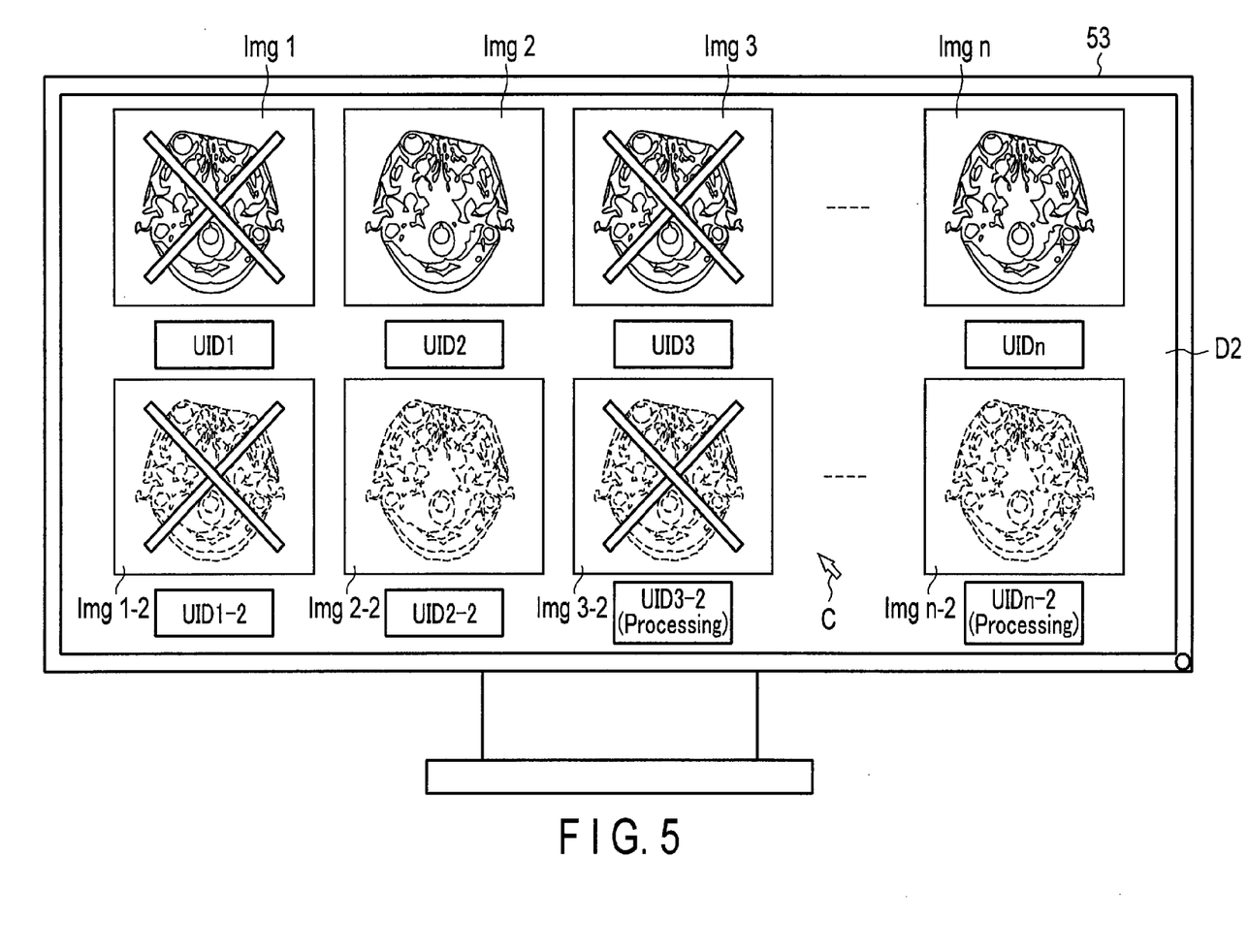
FIG. 5 is a diagram showing an example of a display of a CT image displayed on the display, afterimage display setting by medical image interpretation apparatus control circuitry.

FIG. 5 is a diagram showing an example of a display of a CT image displayed in the display 53, after image display setting by the medical image interpretation apparatus control circuitry 55. As shown in FIG. 5, the display 53 displays, on a display window D2, CT images Img 1 to Img n transferred from the CT console 4, and processed image Img 1-2 to Img n-2 generated from the CT images by the clinical application in the medical image interpretation apparatus 5. The CT images Img 1 to Img n are respectively assigned UID1 to UIDn. The processed images Img 1-2 to Img n-2 are respectively assigned UID1-2 to UIDn-2. For example, as shown in FIG. 5, if the CT image Img 1 is determined to be unsuitable for image interpretation in the CT console 4, the medical image interpretation apparatus control circuitry 55 specifies the CT image Img 1 of the UID1 based on the transferred image inspection result (unsuitable for image interpretation) and the UID. Furthermore, the medical image interpretation apparatus control circuitry 55 reads an image interpretation unsuitable mark from the storage 54. The medical image interpretation apparatus control circuitry 55 displays the read image interpretation unsuitable mark in addition to the CT image Img 1 of the UID1, so that the CT image cannot be selected by the cursor C. The medical image interpretation apparatus control circuitry 55 also displays the image interpretation unsuitable mark in addition to the processed image Img 1-2 of the UID1-2 generated from the CT image that is unsuitable for the image interpretation, so that the processed image cannot be selected by the cursor C. If the CT image Img3 of the UID3 is also determined to be unsuitable for image interpretation, the medical image interpretation apparatus control circuitry 55 reads the image interpretation unsuitable mark from the storage 54. The medical image interpretation apparatus control circuitry 55 displays the read image interpretation unsuitable mark with the CT image Img 3, so that the CT image cannot be selected by the cursor C. The medical image interpretation apparatus control circuitry 55 also displays the image interpretation unsuitable mark with the processed image Img 3-2 of the UID3-2, which is being generated from the CT image Img 3 that is unsuitable for the image interpretation, so that the processed image cannot be selected by the cursor C. Furthermore, generation of the processed image Img 3-2 of the UID3-2 in the medical image interpretation apparatus control circuitry 55 is stopped.

From step Sa11 to step Sa14, the medical image interpretation apparatus control circuitry 55 displays an image interpretation operation window as the image interpretation function 553. The image interpreting doctor operates the image interpretation operation window by the input interface circuitry 51 and selects a target CT image to be subjected to image interpretation from the CT images that are determined to be "suitable for image interpretation", and starts image interpretation of the selected CT image. After the image interpretation, the image interpreting doctor generates an image interpretation report in the medical image interpretation apparatus 5.

According to the configuration described above, the medical image management system of the embodiment transfers all images to the medical image interpretation apparatus 5 before completion of the image inspection performed after completion of the imaging. Furthermore, the medical image interpretation apparatus 5 starts processing by a clinical application to enable image interpretation. To avoid referring to or storing an unnecessary image, image inspection progress information indicating that the image is being inspected is added to the image during transference. After the image inspection, the image inspection progress information is updated based on image inspection progress information transferred from the CT console 4. The user of the medical image interpretation apparatus 5 can determine whether image interpretation can be started, or the image interpretation can be continued, on the basis of the display-set image upon an update of the image inspection progress information.

As a result, the time length from the medical imaging to the image transfer and utilization by the image interpreting doctor can be reduced, while unnecessary image interpretation or unnecessary image storage is avoided.

(Modification 1)

Figure 6:
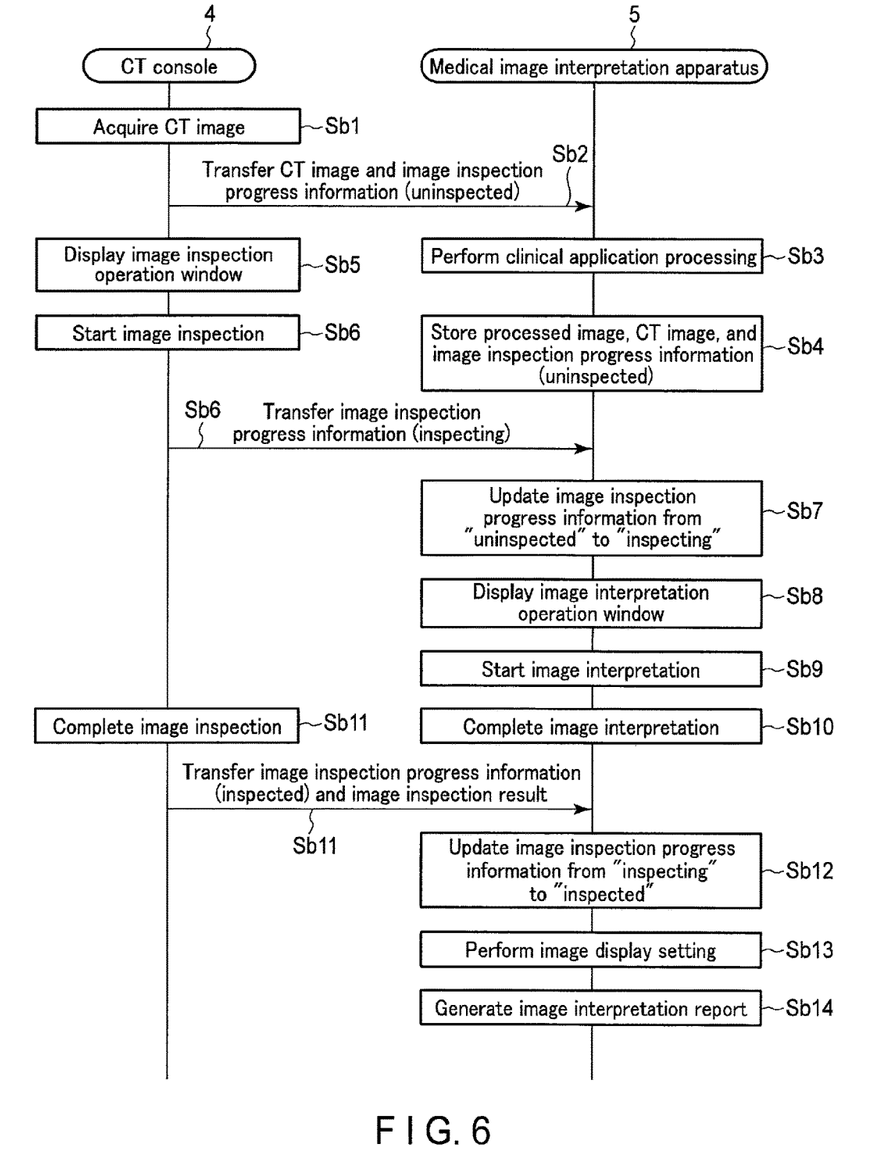
FIG. 6 is a flowchart showing a flow from CT image acquisition to generation of a medical image interpretation report in modification 1.

In the embodiment described above, image interpretation is performed after completion of image inspection. However, the embodiment is not limited to this aspect. In the medical image management system of this embodiment, the image interpretation may be started during image inspection and the inspection result may be reflected in the image after the image interpretation, as shown in FIG. 6. The steps overlapping those shown in FIG. 3 will be described if necessary.

As shown in FIG. 6, in step Sb6, the CT apparatus control circuitry 47 transfers image inspection progress information (inspecting) to the medical image interpretation apparatus 5 after starting the image inspection. In step Sb7, the medical image interpretation apparatus control circuitry 55 updates the image inspection progress information stored in the storage 54 from "uninspected" to "inspecting", based on the image inspection progress information (inspecting) transferred from the CT console 4 as the update function 551. In steps Sb8 to Sb10, the medical image interpretation apparatus control circuitry 55 displays an image interpretation operation window as an image interpretation function 553. The image interpreting doctor operates the image interpretation operation window by the input interface circuitry 51 and selects a target CT image to be subjected to image interpretation, and starts image interpretation of the selected CT image.

In step Sb11, after completion of the image inspection, the CT apparatus control circuitry 47 transfers the current image inspection progress information (inspected) and an image inspection result to the medical image interpretation apparatus 5. In step Sb12, the medical image interpretation apparatus control circuitry 55 updates the image inspection progress information stored in the storage 54 from "inspecting" to "inspected" based on the image inspection progress information (inspected) transferred from the CT console 4 as the update function 551. In step Sb13, upon updating the image inspection progress information stored in the storage 54 from "inspecting" to "inspected", the medical image interpretation apparatus control circuitry 55 performs image display setting for the CT image stored in the storage 54 based on the transferred image inspection result as the image display setting function 552.

Accordingly, even after completion of the image interpretation, the image inspection result can be reflected as a follow-up, and a CT image or the corresponding processed image, suitable for image interpretation, can be displayed, while a CT image or the corresponding processed image, unsuitable for image interpretation, is not displayed.

In the embodiment described above, as shown in FIG. 6, the image inspection progress information (inspected) and the inspection result are transferred from the CT console 4 to the medical image interpretation apparatus 5 after completion of the image interpretation. However, the embodiment is not limited to this aspect. For example, the image inspection progress information (inspected) and the image inspection result may be transferred from the CT console 4 to the medical image interpretation apparatus 5 during a time between the start and the completion of image interpretation.

The reflection of the image inspection result may be an update of meta-information, reprocessing of the clinical application, etc., which may be performed either automatically or manually. Furthermore, to avoid reprocessing of the clinical application, operations may be restricted. For example, only reference to an image unsuitable for image interpretation may be allowed, while storage of a generated image or generation of an image interpretation report on the basis of an image under inspection may be prohibited.

(Modification 2)

Figure 7:
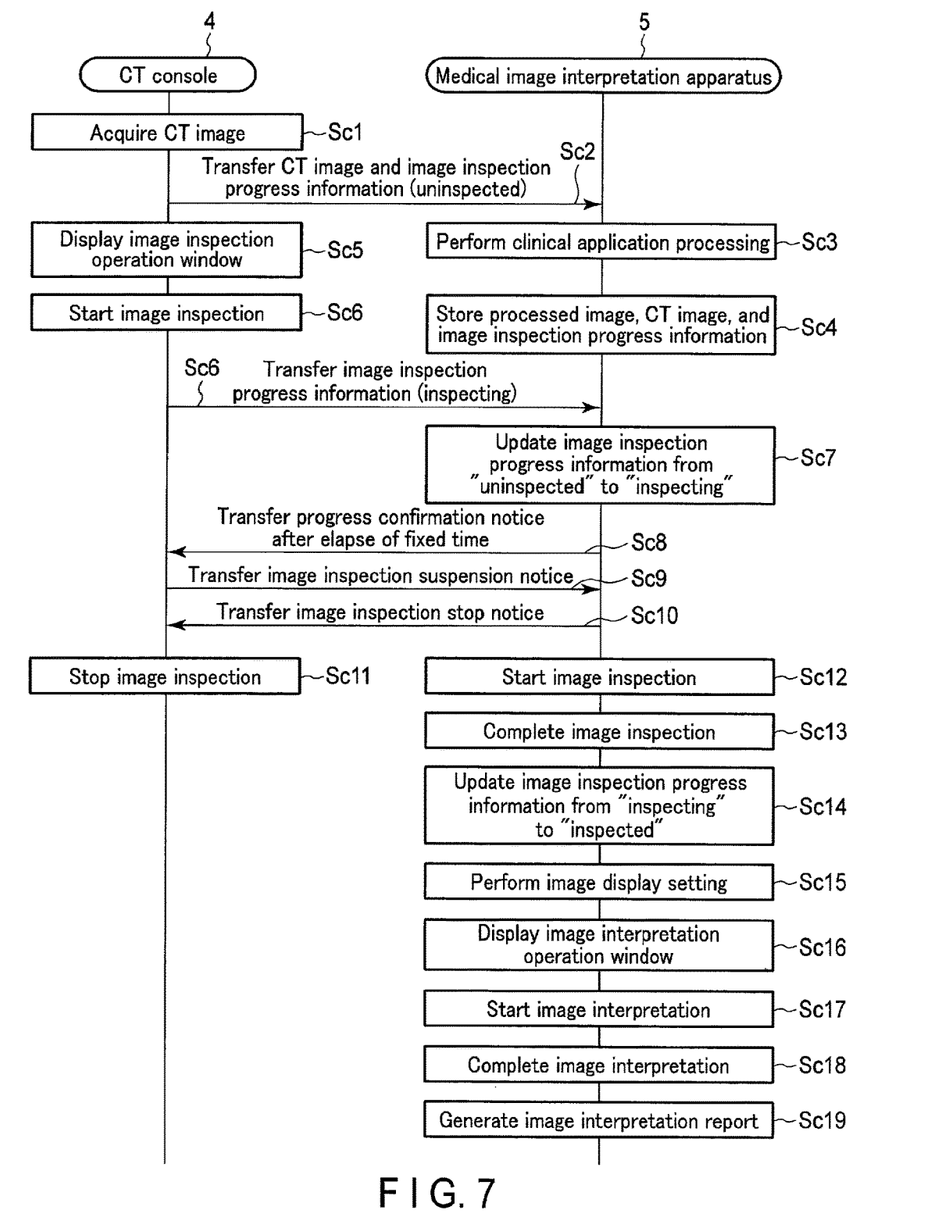
FIG. 7 is a flowchart showing a flow from CT image acquisition to generation of a medical image interpretation report in modification 2.

In the embodiment described above, image inspection is performed in the CT console 4; however, the embodiment is not limited to this aspect. In the medical image management system of this embodiment, as shown in FIG. 7, if the image inspection in the CT console 4 requires considerable time, and image interpretation cannot be performed immediately, the image inspection may be performed in the medical image interpretation apparatus 5. The steps overlapping those shown in FIG. 3 and FIG. 6 will be described if necessary.

As shown in FIG. 7, in step Sc6, after starting of the image inspection, the CT apparatus control circuitry 47 transfers the image inspection progress information (inspecting) to the medical image interpretation apparatus 5. In step Sc7, the medical image interpretation apparatus control circuitry 55 updates the image inspection progress information stored in the storage 54 from "uninspected" to "inspecting" based on the transferred image inspection progress information (inspecting) as the update function 551. Thereafter, if the image inspection progress information (inspecting) and the image inspection result are not transferred from the CT console 4 to the medical image interpretation apparatus 5 after the elapse of a fixed time due to a malfunction of the CT console 4 or absence of the radiology technologist, the medical image interpretation apparatus control circuitry 55 transfers a progress confirmation notice to the CT console 4 in step Sc8. In step Sc9, the CT apparatus control circuitry 47 transfers an image inspection suspension notice indicating that the image inspection is suspended to the medical image interpretation apparatus 5. In step Sc10, upon receipt of the image inspection suspension notice transferred from the CT console 4, the medical image interpretation apparatus control circuitry 55 displays in the display 53 a confirmation window to request the user of the medical image interpretation apparatus 5 (for example, the image interpreting doctor) to confirm whether image interpretation is urgently needed. If the user of the medical image interpretation apparatus 5 instructs that image interpretation is urgently needed via the input interface circuitry 51, the medical image interpretation apparatus control circuitry 55 transfers an image inspection stop notice to the CT console 4. In step Sc11, upon receipt of the image inspection stop notice transferred from the medical image interpretation apparatus 5, the CT apparatus control circuitry 47 stops the image inspection currently under operation. In step Sc12, the medical image interpretation apparatus control circuitry 55 performs image inspection of the transferred CT image.

Thus, even if the image inspection in the CT console 4 requires considerable time, and image interpretation cannot be performed immediately, the image inspection can be performed in the medical image interpretation apparatus 5. As a result, the medical image interpretation apparatus 5 can determine a CT image suitable for image interpretation or a CT image unsuitable for image interpretation.

(Modification 3)

Figure 8:
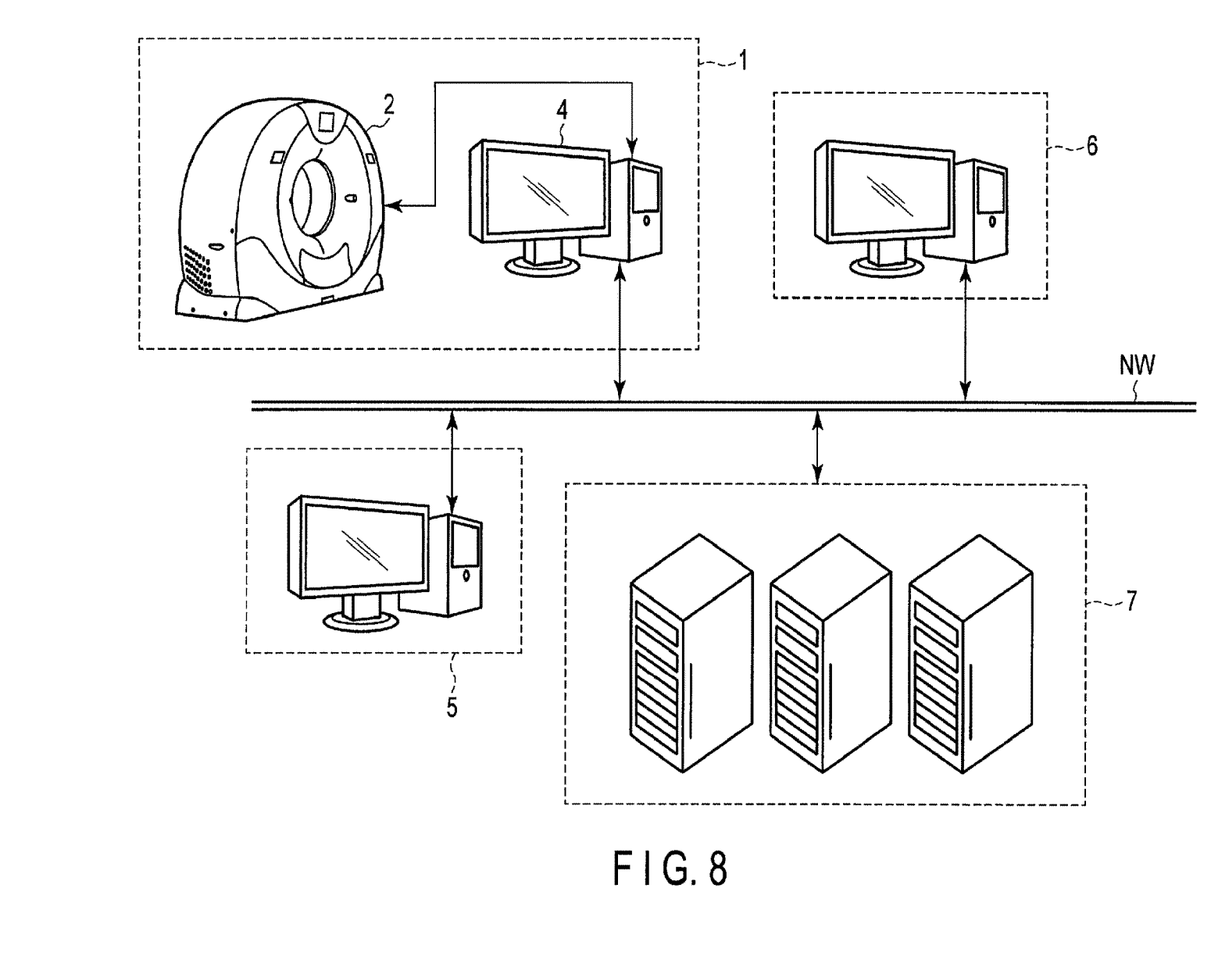
FIG. 8 is a diagram showing a medical image management system according to an embodiment in modification 3.

In the embodiment described above, image inspection is performed in the CT console 4 in the X-ray CT apparatus 1, and the image is directly transferred to the medical image interpretation apparatus 5. However, the embodiment is not limited to this aspect. As shown in FIG. 8, the picture archiving and communication system of this embodiment may include a medical image inspection apparatus 6 that is separately set to perform image inspection, and a picture archiving and communication apparatus 7 that archives medical images. The picture archiving and communication apparatus 7 is a server that forms a PACS (Picture Archiving and Communication System). For example, medical images acquired by the medical image diagnosis apparatus 1 may be transferred to the medical image inspection apparatus 6, and image inspection may be performed in the medical image inspection apparatus 6. Furthermore, medical images acquired by the medical image diagnosis apparatus 1 may be archived in the picture archiving and communication apparatus 7, and may be read by the medical image display apparatus 5 each time image interpretation is performed.

(Closing)

As described above, in the medical image management system of the embodiment, the medical image interpretation apparatus 5 acquires at least one medical image acquired by imaging a subject by a medical imaging apparatus, and image inspection progress information (inspecting) indicating that image inspection of the medical image is being performed in the CT console 4. The medical image interpretation apparatus 5 acquires image inspection progress information (inspected) indicating that the image inspection of the medical image is completed. If the medical image interpretation apparatus 5 acquires the image inspection progress information (inspected), it updates the image inspection progress status from "inspecting" to "inspected".

With the above configuration, the medical image management system of the embodiment performs image inspection of a medical image in the CT console 4 in parallel with processing in the medical image interpretation apparatus 5 by a clinical application, and image interpretation can be performed immediately after completion of the image inspection.

Thus, the medical image management system of the embodiment can improve throughput in medical examination.

The term "predetermined processor" in the above description means, for example, a special purpose or general purpose processor, circuitry, processing circuitry, operation circuitry, arithmetic circuitry, or Application Specific Integrated Circuit (ASIC), a programmable logical device (for example, a Simple Programmable Logic Device (SPLD), a Complex Programmable Logic Device (CPLD), and a Field Programmable Gate Array (FPGA)), etc. Each of the components (processing circuitry) of the embodiment is not limited to a single processor, but may be realized by a plurality of processors. Furthermore, a plurality of components (a plurality of processing circuitry) may be realized by a single processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image display apparatus for image interpretation comprising:
   reception circuitry configured to
      receive a plurality of medical images imaged by a medical imaging apparatus before performing image inspection corresponding to an operation to confirm whether the medical images are available for the image interpretation,
      receive first progress information corresponding to each of the medical images, the first progress information indicating that image inspection for each of the medical images is in progress in a medical image inspection apparatus, and receive second progress information corresponding to each of the medical images, the second progress information indicating completion of the image inspection for each of the medical images;

a storage configured to store the medical images and the first progress information;

control circuitry configured to update, if the second progress information is received, the stored first progress information to the received second progress information regarding each of the medical images corresponding to the received second progress information, perform, if the first progress information is updated to the second progress information, a predetermined process for a medical image corresponding to the updated second progress information among the medical images in accordance with a result of the image inspection, and control a display to display the medical image determined to be suitable for image interpretation in the medical image inspection apparatus among the medical images stored in the storage; and not display the medical image determined to be unsuitable for image interpretation in the medical image inspection apparatus among the medical images stored in the storage; and the display configured to display only the medical image suitable for image interpretation.

2. The medical image display apparatus according to claim 1, wherein the control circuitry adds first additional information to the medical image determined to be unsuitable for image interpretation, and adds second additional information to the medical image determined to be suitable for image interpretation, and wherein the medical image to which the first additional information is added is unsuitable for image interpretation, and the medical image to which the second additional information is added is suitable for image interpretation.

3. The medical image display apparatus according to claim 2, wherein the control circuitry deletes the medical image determined to be unsuitable for image interpretation stored in the storage.

4. The medical image display apparatus according to claim 1, wherein the control circuitry controls the display to display second display information with the medical image determined to be suitable for image interpretation, and wherein the medical image displayed on the display with the second display information is suitable for image interpretation.

5. A medical image management system comprising a medical image processing apparatus and a medical image display apparatus for image interpretation connected via a network, the medical image processing apparatus comprising:

processing circuitry configured to perform image inspection of a plurality of medical images imaged by a medical imaging apparatus; and transfer circuitry configured to transfer the plurality of medical images to the medical image display apparatus before performing the image inspection corresponding to an operation to confirm whether the medical images are available for the image interpretation, transfer first progress information corresponding to each of the medical images to the medical image display apparatus, the first progress information indicating that the image inspection for the each of the medical images is in progress in the processing circuitry, and transfer second progress information corresponding to each of the medical images to the medical image display apparatus, the second progress information indicating completion of the image inspection for each of the medical images; and the medical image display apparatus comprising:

reception circuitry configured to receive the medical images, the first progress information, and the second progress information, which are transferred from the medical image processing apparatus;

a storage configured to store the medical images and the first progress information;

control circuitry configured to update, if the second progress information is received, the stored first progress information to the received second progress information regarding each of the medical images corresponding to the received second progress information, perform, if the first progress information is updated to the second progress information, a predetermined process for a medical image corresponding to the updated second progress information among the medical images in accordance with a result of the image inspection, and control a display to display the medical image determined to be suitable for image interpretation in the medical image inspection apparatus among the medical images stored in the storage; and not display the medical image determined to be unsuitable for image interpretation in the medical image inspection apparatus among the medical images stored in the storage; and the display configured to display only the medical image suitable for image interpretation.

* * * * *